United States Patent [19]
Garland et al.

[11] 3,962,291
[45] June 8, 1976

[54] TOTAL SYNTHESIS OF 11-ALKYL STEROIDS

[75] Inventors: Robert B. Garland, Northbrook; Raphael Pappo, Skokie, both of Ill.

[73] Assignee: G. D. Searle & Co., Chicago, Ill.

[22] Filed: Sept. 5, 1974

[21] Appl. No.: 503,270

[52] U.S. Cl. .......................... 260/397.45; 260/397.5
[51] Int. Cl.² .............................................. C07J 1/00
[58] Field of Search ................................ 260/397.45

[56] References Cited
UNITED STATES PATENTS 3,723,483  3/1973  Coombs ........................ 260/397.45
3,876,670  4/1975  Coombs ........................ 260/397.45

OTHER PUBLICATIONS

"Experimentia," vol. 26, No. 7, (1970), pp. 762–763.

*Primary Examiner*—Elbert L. Roberts
*Attorney, Agent, or Firm*—John A. Dhuey; Elliot N. Schubert

[57] ABSTRACT

A novel total synthesis of 11-alkyl steroids, utilizing readily available and inexpensive raw materials, is described. The resulting products are useful and novel pharmacological agents possessing, for example, selective hormonal properties.

2 Claims, No Drawings

TOTAL SYNTHESIS OF 11-ALKYL STEROIDS

The present invention is concerned with a novel total synthesis of 11-alkyl steroids and with novel 11-alkyl steroids produced thereby. These novel compounds are particularly useful in consequence of their valuable pharmacological properties, e.g. progestational, and possess the further advantage of exhibiting minimal undesirable hormonal side-effects, e.g. estrogenic.

The aforementioned novel and useful 11-alkyl steroids are represented by the following structural formula

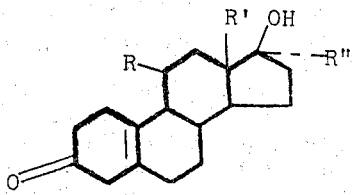

wherein R is a lower alkyl radical, R' is a lower alkyl radical containing more than one carbon atom and R'' is a lower 1-alkynyl radical.

The term lower alkyl radical comprehends those groups containing up to and including 7 carbon atoms and is exemplified by methyl, propyl, pentyl, heptyl and the corresponding branched-chain radicals.

Representative of the 1-alkynyl radicals comprehended are ethynyl, 1-propynyl, 1-hexynyl, 1-heptynyl and the branched-chain isomeric groups corresponding.

The novel process of the present invention utilizes, as the starting material, a 6-alkoxy-1-tetralone. Reaction of that substance with a suitable organo-metallic reagent affords the desired 1-substituted-1-tetralol, which is dehydrated, then quaternized or, optionally quaternized then dehydrated to afford the corresponding 6-alkoxy-1-substituted 3,4-dihydronaphthalene derivative. Reaction of the latter substance with a 2-alkyl-cyclopentane-1,3-dione, in the presence of sodium methoxide and hexamethylphosphoramide, affords the 2-(6-alkoxy-3,4-dihydro-1-naphthyl)-3-(2-alkylcyclopentane-1,3-dion-2-yl)propene, which is heated in the presence of a suitable proton source, e.g. p-toluene sulfonic acid, to produce, in the dl form, a 3-alkoxy 11-alkylene-8,14-bisdehydro-13-alkylgona-1,3,5(10)-trien-17-one. Subsequent reductions of the 8 and 14 unsaturated linkages and the 17-keto group result in the d,1-11$\beta$,13$\beta$-dialkylgona-1,3,5(10)-triene-3,17$\beta$-diol 3-alkyl ethers. Reduction of the aromatic A-ring system, typically with sodium in liquid ammonia, affords the 2,5(10)-3-enol ether, which is oxidized, suitably with chromic acid, to produce the desired corresponding 17-ketone. Alkynylation, for example, with acetylene followed by cleavage of the enol ether function affords the novel aforementioned progestational compounds of the following formula

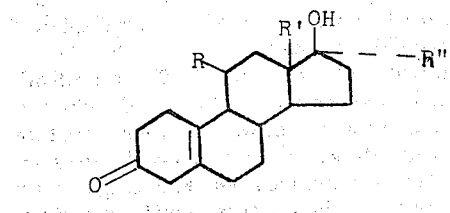

wherein R, R' and R'' are as hereinfefore defined. Rearrangement of the $\Delta^{5(10)}$ double bond to the $\Delta^4$ position affords compounds also useful as progestational agents. Reduction of the 3-keto function produces compounds useful as luteolytic agents as are the corresponding bis-alkanoates.

The progestational activity of the aforementioned compounds of this invention is demonstrated by their ability to induce proliferation of the lumenal epithelium of the uterus. A suitable assay for detection of this property is described by Clauberg, C. Zentr. Gynakol., 54, 2757(1930).

The invention will appear more fully from the examples which follow. These examples, however, are given by way of illustration only and are not to be construed as limiting the invention either in spirit or in scope as many modifications both in materials and in methods will be apparent to those skilled in the art. In these examples, quantities of materials are given in parts by weight except where other wise noted and temperatures are denoted in degrees Centigrade (°C.).

EXAMPLE 1

Following the procedure described by Bar, Marcinal and Marcinal-Le-Febvre, Bull. Soc. Chim. (France) 1972, 2484, a Grignard Reagent is prepared, using 40 parts of 2-bromo-N, N-dimethyl-allylamine, 6 parts of magnesium and 300 parts by volume of tetrahydrofuran. The resulting solution is cooled to 0°–5° and 26.5 parts of 6-methoxy-tetralone dissolved in 100 parts by volume of tetrahydrofuran is added over a period of about 15 minutes. The resulting reaction mixture is heated at the reflux temperature for about 1 hour, then is partially concentrated by distillation under reduced pressure. The mixture is cooled and diluted with ether and the resulting organic mixture is treated with 300 parts by volume of ice-cold saturated aqueous ammonium chloride. That twophase system is extracted twice with ether and the ether solutions are combined, then washed with 5% aqueous ammonium hydroxide and finally twice with water. Drying of the organic solution over anhydrous sodium sulfate followed by removal of the solvent results in the desired product, 6-methoxy-1-(3-dimethylaminopropen-2 -yl)-1-tetralol, which after chromatographic purification on basic alumina followed by elution with 10% ether in benzene, is characterized by ultraviolet absorption maxima at about 276 and 283 millimicrons with molecular extinction coefficients of about 1620 and 1570, respectively.

EXAMPLE 2

To a solution containing 15 parts of crude 6-methoxy-1-(3-dimethylaminopropen-2-yl)-1-tetralol, (which contains approximately 50% of 6-methoxy-1-tetralone), dissolved in 400 parts by volume of ether is added 20 parts of methyliodide. The resulting solution is stored in the dark for about 5 days, during which time the product separates slowly. The resulting solid is collected by filtration, washed with ether and recrystalized from methanol-ether to afford ord 6-methoxy-1-(3-dimethylaminopropen-2-yl)-1-tetralol methiodide, melting at about 140°–144°. Ultraviolet absorption maxima are observed at about 220, 275 and 283 millimicrons with molecular extinction eoefficients of about 23,200, 2780 and 2540, respectively.

EXAMPLE 3

A suspension consisting of 4.03 parts of 6-methoxy-1-(3-dimethylaminopropen-2-yl)-1-tetralol methiodide in 25 parts by volume of acetic acid and 1 part by volume of acetic anhydride is stirred for about 16 hours and the resulting solution is then conventrated under reduced pressure to afford a residual solid. That material is dissolved in methanol and water is added to the point of incipient turbidity. The resulting mixture is then concentrated to dryness and the residue is recrystallized from isopropyl alcohol to afford 6-methoxy1-(3-dimethylaminopropen-2-yl)-3,4-dihydronaphtalene methiodide melting at about 175°–178°. This compound exhibits ultraviolet absorption maxima at about 218 and 268 millimicrons with molecular extinction coefficients of approximately 27,560 and 10,000, respectively.

EXAMPLE 4

To a solution containing 326 parts of 2-bromopropenyldimethylamine in 1200 parts by volume of hexane is added, at −40°, a solution consisting of two molecular equivalents of n-butyllithium in hexane over a period of about 45 minutes. The resulting reaction mixture is stirred for 30 minutes longer, at the end of which time a solution containing 300 parts of 6-methoxy-1-tetralone in 1500 parts by volume of benzene is added at a temperature between −40 and −30°. That mixture is then allowed to warm to approximately 0° and 500 parts of water is added cautiously. The organic layer is separated, washed several times with water, then extracted with dilute hydrochloric acid. The acidic layers are washed with ether, then cooled to 0° and made strongly basic by the addition of cold aqueous 50% sodium hydroxide. The amine thus liberated is extracted into ether and that ether solution is washed with dilute aqueous sodium hydroxide, then with saturated aqueous sodium chloride. Drying of the organic solution over sodium sulfate is followed by distillation of the solvent under reduced pressure, thus affording 6-methoxy-1-(3-dimethylaminopropen-2-yl)-3,4-dihydronaphthalene), which is purified by distillation under reduced pressure, specifically at 0.3 millimeters pressure, whereat it exhibits a boiling point of 143°–148°. Conversion of that amine, which exhibits an ultraviolet absorption maximum at about 273 millimicrons with a molecular extinction coefficient of about 10,900, to the corresponding hydrochloride affords a crystalline product, melting at about 175°–176°.

EXAMPLE 5

To a solution of 160 parts of 6-methoxy-1-(3-dimethylaminopropen-2-yl)-3,4-dihydrophthalene) in 3,000 parts by volume of benzene is added 100 parts of methyl iodide and the resulting reaction mixture is stirred at room temperature for about 16 hours. The resulting crystalline product is collected by filtration, washed on the filter with benzene and dried to afford 6-methoxy-1-(3-dimethylaminopropen-2-yl)-3,4-dihydronaphthalene, methiodide melting at about 180°–182° and displaying ultraviolet absorption maxima at about 218 and 269 millimicrons with molecular extinction coefficients of about 28,000 and 10,200, respectively.

EXAMPLE 6

A solution consisting of 68.8 parts of 6-methoxy-1-(3-dimethylaminopropen-2-yl)-3,4-dihydronaphthalene) and 80 parts of methyl p-toluenesulfonate in 1700 parts by volume of benzene is stored at room temperature for about 3 days, at the end of which time 200 parts by volume of cyclohexane is added and the solution is cooled to approximately 0°–5°. The resulting solid is collected by filtration, washed with cyclohexane and dried to afford 6-methoxy-1-(3-dimethylaminopropen-2-yl)-3,4dihydronaphthalenemethyl p-toluenesulfonate, melting at about 148°–150°.

EXAMPLE 7

A solution containing 41.5 parts of 6-methoxy-1-(3-dimethylaminopropen-2-yl)-3,4-dihydronaphthalenemethyl p-toluenesulfonate dissolved in 200 parts by volume of 50% aqueous methanol is passed through an ion exchange column containing 100 parts of Amberlite IRA 400 ion exchange resin, in the hydroxide form, and that column is then eluted with 50% aqueous methanol until the eluants are no longer alkaline. To this solution is then added 12 parts of 2-methylcyclopentane-1,3-dione and that solution is concentrated to a small residue, at which time 250 parts by volume of benzene is added. The resulting mixture is heated at the reflux temperature and the water of reaction is continuously separated. At that time 200 parts by volume of diethylene glycol dimethylether, 400 parts by volume of xylene and 5 parts by volume of triethylamine are added and the reaction mixture is distilled slowly until the temperature of the mixture reaches 135°. At that time the mixture is heated at the reflux temperature for about 20 hours, then concentrated to a small residue under reduced pressure. The resulting residue is extracted into benzene and the benzene layer is washed successively with water, dilute hydrochloric acid, water, dilute aqueous sodium bicarbonate and finally with water. Drying of that solution over anhydrous sodium sulfate followed by concentration to dryness under reduced pressure affords the crude product, which is purified by recrystallization from cyclohexane then from methanol to yield 2-(6-methoxy-3,4-dihydro-1-naphthyl)-3-(2-methylcyclopentane-1,3-dione-2-yl)propene, melting at about 81°–82° and displaying an ultraviolet absorption maximum at about 274 millimicrons with a molecular extinction coefficient of about 10,400.

EXAMPLE 8

To a solution containing 4.52 parts of 2-methylcyclopentane-1,3-dione dissolved in 100 parts by volume of methanol is added 2.18 parts of sodium methoxide. To that mixture is then added 750 parts by volume of dry xylene and the mixture is distilled slowly until the boiling point reaches approximately 138°. The mixture is cooled in 11.42 parts of 6-methoxy-1-(3-dimethylaminopropen-2-yl)-3,4-dihydronapthalene methiodide and 25 parts by volume of hexamethylphosphoramide are added. That mixture is heated to the boiling point and approximately 50 parts by volume of distillate is collected. Refluxing is continued for approximately 20 hours, at the end of which time the mixture is cooled, washed with water, dilute hydrochloric acid, water, 5% aqueous sodium bicarbonate and again with water. Drying of that solution over anhydrous sodium sulfate followed by removal of the solvent by distillation under reduced pressure affords a residue, which is purified by chromatographic adsorption on silica gel and finally by crystallization from methanol to yield 2-(6-methoxy-3,4-dihydro- 1-naphthyl)-3-(2-methylcyclopentane-1,3-dione-2-yl)propene, melting at about 81°–82° and displaying an ultraviolet absorption maximum of about 275 millimicrons with a molecular extinction coefficient of about 10,200.

EXAMPLE 9

To a solution containing 13.3 parts of 2-(6-methoxy-3,4-dihydro-1-naphthyl)-2-propen-1-yl trimethylammonium iodide in 200 parts by volume of methanol and 1 part by volume of water is added 4.1 parts of silver oxide and the resulting reaction mixture is stirred for approximately 2 hours. At the end of that time the mixture is filtered into a container holding 4 parts of 2-methylcyclopentane-1,3-dione. The resulting solution is concentrated to a small volume and 500 parts by volume of xylene, 5 parts by volume of hexamethylphosphoramide and 5 parts by volume of triethylamine are added. Approximately 50 parts by volume of solvent is removed by distillation and the resulting mixture is heated gently at the reflux temperature for about 20 hours, then allowed to cool. That solution is washed successively with water, 5% hydrochloric acid, water, 5% aqueous sodium bicarbonate and water again, after which time the mixture is dried over anhydrous sodium sulfate and concentrated to a small residue. Crystallization of that crude product from methanol affords 2-(6-methoxy-3,4-dihydro-1-naphthyl)-3-(2-methylcyclopentane-1,3-dione-2-yl)propene, melting at about 81°–82° and displaying an ultraviolet absorption at about 274 millimicrons with a molecular extinction coefficient of approximately 10,400.

EXAMPLE 10

A solution prepared by refluxing 2.85 parts of p-toluene sulfonic acid monohydrate in 400 parts by volume of benzene under a water separator is cooled to room temperature and added slowly to a cooled solution consisting of 4.7 parts of 2-(6-methoxy-3,4-dihydro-1-naphthyl)-3-(2-methylcyclopentane-1,3-dione-2-yl)propene in 50 parts by volume of toluene, while the temperature is maintained at approximately 0–5°. Approximately 10 minutes after addition is complete, 100 parts of ice water is added. The organic layer is separated, washed several times with water, then with saturated aqueous sodium chloride. Drying over anhydrous sodium sulfate followed by removal of the solvent by distillation under reduced pressure affords the crude product, which is purified by trituration with methanol, thus affording, after recrystallization from methylene chloride-methanol, d,1-11-methylene-8,14-bisdehydroestrone-3-methyl ether, melting at about 161°–163° and displaying ultraviolet absorption maxima at about 246, 255, 325, 313 and 338 millimicrons with molecular extinction coefficients of approximately 15,200, 12,700, 23,700, 20,400 and 19,300, respectively.

EXAMPLE 11

To a solution of 2.23 parts of d,1-11-methylene8,14-bisdehydroestrone-3-methyl ether in 20 parts by volume of benzene and 50 parts by volume of ether is added 5 parts by volume of 0.9 M lithium aluminum hydride and ether. After a period of 10 minutes, the excess reducing agent is decomposed by a reaction with water and the resulting mixture is washed first with dilute hydrochloric acid, then with water. After drying over anhydrous sodium sulfate, the solvents are removed by distillation under reduced pressure and the resulting residue is recrystallized from ether to afford, as the methanol solvate, d,1-11-methylene-8,14-bisdehydroestradiol-3-methyl ether, melting at about 102°–110°. Recrystallization from boiling hexane, then from ether affords the pure product, melting at about 120°–124°, and exhibiting ultraviolet absorption maxima at about 248, 257, 312, 325 and 339 millimicrons with molecular extinction coefficients of about 12,900, 11,000, 16,900, 19,000 and 15,400, respectively.

EXAMPLE 12

A solution containing 0.41 parts of d,1 11-methylene-8,14-bisdehydroestradiol-3-methyl ether and 40 parts by volume of benzene is shaken with hydrogen at amospheric pressure and room temperature in the presence of 0.05 part of a 5% palladium-on-calcium carbonate catalyst until 1 equivalent of hydrogen is absorbed. At the end of that time the catalyst is removed by filtration and the solvent by distillation and crystallization of the residue from aqueous material affords d,1-11-methyl8(14),9(11)-bisdehydroestradiol 3-methyl ether, melting at about 124°–127° and displaying ultraviolet absorption maxima at approximately 244, 285 and 250 millimicrons with molecular extinction coefficients of 20,800, 7,600 and 20,500 respectively.

EXAMPLE 13

A solution consisting of 0.312 parts of d,1-11-methyl8(14),9(11)-bisdehydroestradiol3-methyl ether and 20 parts by volume of benzene is shaken with hydrogen at atmospheric pressure and room temperature in the presence of 0.156 part of a 5% palladium-on alumina catalyst is removed by filtration and the solvent by distillation. The resulting residue is purified by recrystallization from aqueous methanol to yield d,1-11β-methyl-8-dehydroestradio-3-methyl ether, melting at about 158°–161°. Ultraviolet absorption maxima are observed at about 270 and 278 millimicrons with molecular extinction coefficients of approximately 13,600 and 13,900, respectively.

EXAMPLE 14

A solution containing 1.48 parts of d,1-11-methylene-8,14-bisdihydroestadiol 3-methyl ether in 50 parts by volume of ethanol is skaken with hydrogen in the presence of 0.74 part of 5% palladium-on-alumina catalyst at room temperature at atmospheric pressure until 2 equivalents of hydrogen are absorbed. At the end of that time the catalyst is removed by filtration and the solvent is removed by distillation. Purification of that crude product from methanol affords, d,1-11βmethyl-8-dehydroestradiol 3-methyl ether, melting at about 159°–161° and exhibiting ultraviolet absorption maxima at about 270 and 278 millimicrons with molecular extinction coefficients of approximately 13,600 and 13,900, respectively.

EXAMPLE 15

To a solution of 0.55 parts of sodium metal and approximately 50 parts by volume of anhydrous liquid ammonia is added a solution consisting of 0.253 part of d,1-11β-methyl-8-dehydroestradiol-3-methyl ether in 5 parts by volume of aniline and 20 parts by volume of tetrahydrofuran. That reaction mixture is stirred for approximately 30 minutes, at the end of which time 1 part of solid ammonium chloride is added. The ammonia is then allowed to evaporate and the residue is heated in a steam bath at approximately 60° under a stream of nitrogen for about 1 hour. When the mixture is at room temperature, 50 parts by volume of 5% hydrochloric acid is added and stirring is continued until formation of the crystals is complete. Those crystals are collected by filtration and washed well with water, then purified by recrystallization from aqueous methanol to afford d,1-11β-methylestradiol3-methyl ether, melting at about 143°–145° and displaying ultraviolet absorption maxima at about 279 and 288 millimicrons with molecular extinction coefficients of approximately 1,920 and 1,880, respectively.

EXAMPLE 16

A solution containing 0.132 parts of d,1-11β-methylestradiol-3-methyl ether in 10 parts by volume of acetone is treated with a slight excess of 8 Normal chromic acid solution for approximately 2 minutes. At the end of that time the solution is diluted with water and the resulting solid is isolated by filtration, then recrystallized from methanol, thus producing d,1-11β-methylestrone3-methyl ether, melting at about 150°–153° and displaying ultraviolet absorption maxima at about 277 and 286 millimicrons with molecular extinction coefficients of about 2,000 and 1,940, respectively.

EXAMPLE 17

A solution of 13 parts of 2-(6-methoxy-3,4-dihydro-1-naphthyl)-2-propen-1-yltrimethyl ammonium iodide in 200 parts by volume of methanol and 1 part of water is cooled to 0.5° and 4.5 parts of silver oxide is added. The resulting mixture is stirred for about 3 hours and the solid which forms is removed by filtration. At that time 5 parts of 2-ethylcyclopentane-1,3-dione is added to the filtrate. The resulting solution is concentrated to a small volume and 400 parts by volume of xylene together with 2 parts by volume of hexamethylphosphoramide and 5 parts by volume of triethylamine are added. That reaction mixture is slowly distilled to remove water and methanol, in the amount of approximately 50 parts by volume and the resultant mixture is heated at the reflux temperature for about 20 hours. After cooling that mixture is washed with water, 5% hydrochloric acid, water 5% aqueous sodium bicarbonate and the water again. Drying of that solution over anhydrous sodium sulphate followed by removal of the solvent under reduced pressure and crystallization of the resulting residue from methanol affords pure 2-(6-methoxy3,4-dihydro-1-naphthyl)-3-(2-ethylcyclopentane-1,3-dione-2-yl)propene, melting at about 100°–125°. This compound exhibits an ultraviolet absorption maxima at about 273 millimicrons with a molecular extinction coefficient of approximately 11,100.

EXAMPLE 18

A solution prepared from 2.78 parts of p-toluene sulfonic acid monohydrate and 400 parts by volume of benzene by refluxing under a water trap followed by distilling of approximately 100 parts by volume is cooled and then added to a 0° solution consisting of 4.76 parts of 2-(6-methoxy-3,4-dihydro-1-naphthyl)-3-(2-ethylcyclopentane-1-3-dion-2-yl)propene in 75 parts by volume of toluene. The temperature is maintained at 0°–5° during that addition. After approximately 5 minutes 100 parts by volume of ice water is added and the organic layer is separated, washed twice with cold water, then with saturated sodium chloride. After drying over anhydrous sodium sulfate these solvents are removed at approximately 30° and the resulting residue is dissolved in benzene, then passed through a short silica gel column. The solvent is removed and the resulting residue is crystallized from the methanol to afford d,1-11-methylene-18-methyl-8-14-bisdyhydroestrone 3-methyl ether, melting at about 117.5° – 118° and exhibiting ultraviolet absorption maxima at about 247, 256, 326, 314 and 339 millimicrons with molecular extinction coefficients of approximately 15,200, 12,800, 23,700, 20,300 and 19,400, respectively.

EXAMPLE 19

A solution containing 9.36 parts of d,1-11-methylene-18-methyl-8,14-bisdehydroestrone-3-methyl ether and 300 parts by volume of benzene is shaken with hydrogen in the presence of 9 parts of 5% palladium-on-carbon catalyst at atmospheric pressure and room temperature for about 24 hours until 2 equivalents of hydrogen are consumed. The catalyst is removed by filtration and the solvent by distillation under reduced pressure. Purification of that crude product by chromatography on silica gel and finally crystallization from methanol affords d,1-11β, 18-dimethyl8-dehydroesterone-3-methyl ether, melting at about 139°–141° and exhibiting ultraviolet absorption maxima at about 280 and 273 millimicrons with molecular extinction coefficients of approximately 15,400 and 14,900, respectively.

EXAMPLE 20

To a solution containing 1.69 parts of d,1-11β,18-dimethyl-8-dehydroesterone-3-methyl ether in 40 parts by volume of methanol is added 0.075 part of sodium borohydride. After approximately one hour at room temperature, the mixture is treated with 1 part by volume of 50% aqueous acetic acid, then diluted with water and cooled to 0°–5°. The crude product which separates is collected by filtration and purified by recrystallization from cyclohexane, thus affording d,1-11β,18-dimethyl-8-dehydroestradiol3-methyl ether, melting at about 149°–150° and exhibiting ultraviolet absorption maxima at about 277 and 271 millimicrons (shoulder) with molecular extinction coefficients of about 16,400 and 16,900, respectively.

EXAMPLE 21

A solution prepared from 5.53 parts of p-toluene sulfonic acid monohydrate and 500 parts by volume of benzene by refluxing under a water trap and partial concentration is cooled and added to a cold solution containing 8.82 parts of 2-(6-methoxy-3,4-dihydro-1-naphthyl)-3-(2-ethylcyclopentane-1,3-dione-2-yl)propene, keeping the temperature near 0°. After approximately 10 minutes the cold solution is quickly filtered to remove the precipitated p-toluene sulfonic acid monohydrate, then is washed with fresh benzene. The filtrate is diluted with 250 parts by volume of dry ether and 10 parts by volume of 1.3 M lithium aluminum hydride in ether is added. After approximately 15 minutes water is added cautiously to destroy the excess reducing agent and 100 parts by volume of cold hydrochloric acid is added. The organic layer is separated, washed successively with 5% hydrochloric acid, water, and saturated aqueous sodium chloride, then dried over anhydrous sodium sulfate and concentrated to a small residue, which is purified by crystallization from methanol to afford d, 1-11-methylene18-methyl-8,14-bisdehydroestradiol 3-methyl ether, melting at about 87°–88°, and displaying ultraviolet absorption maxima at about 248, 257, 312, 324, and 338 millimicrons with molecular extinction coefficients of about 13,700, 11,300, 19,600, 22,600 and 17,900, respectively

EXAMPLE 22

A solution containing 7.55 parts of d,1-11methylene-18-methyl-8,14-bisdehydroestradiol 3-methyl ether hemimethanolate in 250 parts by volume of methanol is shaken with hydrogen in the presence of 3.7 parts of a 5% palladium-on-alumina catalyst at room temperature under atmospheric pressure until 2 molecular equivalents of hydrogen are absorbed. The catalyst is removed by filtration and the solvent by distillation under reduced pressure. The resulting residue is purified by crystallization from methanol, thus affording d,1-11$\beta$,18-dimethyl8-dehydroestradiol 3-methyl ether, melting at about 131°–142°. Recrystallization from cyclohexane affords pure d,1-11$\beta$,18-dimethyl-8-dehydroestradiol 3-methyl ether, melting at about 154°–155° and displaying ultraviolet absorption maxima at about 278 and 271 millimicrons (shoulder) with molecular extinction coefficients of approximately 17,600 and 17,200, respectively.

EXAMPLE 23

A solution containing 6.11 parts of d,1-11$\beta$,18-dimethyl-8-dehydroestradiol 3-methyl ether in 15 parts by volume of aniline and 100 parts by volume of tetrahydrofuran is added over a period of 5 minutes to a solution consisting of 2.5 parts of sodium metal dissolved in approximately 250 parts by volume of anhydrous liquid ammonia. After a period of 30 minutes, the container is cooled to approximately −70° and 10 parts of solid ammonium chloride is added. When the blue color has been discharged, the mixture is allowed to warm under a stream of nitrogen, then is heated in a 50° steam bath to remove the ammonia. The tetrahydrofuran is removed by distillation under reduced pressure, whereupon 50 parts of water is added to the residue and that mixture is acidified by the addition of dilute hydrochloric acid. The solid formed is collected by filtration and washed with water, then dried over anhydrous sodium sulfate and purified by recrystallization from methanol to afford d,1-11$\beta$,18-dimethylestradiol 3-methyl ether, melting at about 123°–124° and exhibiting ultraviolet absorption maxima at about 220, 278, and 287 millimicrons with molecular extinction coefficients of about 8,250, 2,050 and 1,910.

EXAMPLE 24

A solution containing 0.56 part of d,1-11$\beta$,18-dimethylestradiol 3-methyl ether hemimethanolate in 30 parts by volume of acetone is cooled in an ice bath and then treated with excess 8 Normal chromic acid. After approximately 5 minutes the mixture is diluted with 100 parts of water and the resulting solid is collected by filtration, then washed with water. Recrystallization from aqueous methanol yields d,1-11$\beta$,18-dimethylestrone3-methyl ether, melting at about 144°–145° and exhibiting ultraviolet absorption maxima at about 220, 278 and 286.5 millimicrons with molecular extinction coefficients of approximately 8,390, and 1,970 and 1,900, respectively.

EXAMPLE 25

To a solution of 7 parts of sodium metal and 150 parts by volume of anhydrous ammonia is added over a period of approximately 30 minutes a solution containing 6.2 parts of d,1-11$\beta$,18-dimethylestradiol 3-methyl ether and 75 parts by volume of tetrahydrafuran and 75 parts by volume of isopropyl alcohol. At the end of that time the mixture is allowed to stand for about 1 hour. After the blue color is discharged 2 parts of sodium metal is added. The mixture is again allowed to stand for approximately 90 minutes and the color discharged. At the end of that time 40 parts by volume of methanol is added and the mixture allowed to warm to room temperature, then diluted with approximately 250 parts by volume of water. That mixture is partially concentrated to approximately 200 parts by volume and cooled under nitrogen, at the end of which time the resulting solid is collected by filtration and washed well with water. Drying of that material affords crude d,1-11$\beta$,18-dimethyl-1,4-dihydroestradiol 3-methyl ether, melting at about 155°–158°.

The latter crude product is dissolved in 250 parts by volume of freshly distilled toluene and approximately 50 parts is distilled to assure dryness. After cooling under nitrogen, 60 parts by volume of cyclohexanone is added, followed by 6 parts of aluminum isopropoxide dissolved in 100 parts by volume of dry toluene. That mixture is heated slowly to the reflux temperature for about approximately 1 hour, then is cooled under nitrogen and 45 parts by volume of saturated Rochelle salts solution is added slowly with stirring. The resulting mixture is steam-distilled for approximately 3 hours, then is cooled under nitrogen. That mixture is extracted with ether, washed with water and saturated sodium chloride, then dried over anhydrous sodium sulfate and concentrated dryness under reduced pressure. The resulting residue is triturated with hexane to afford a solid product, melting at about 138°–144°. Recrystallization from cyclohexane-hexane yields d,1-3-methoxy-11$\beta$,18-dimethyl-1,3-dihydroestr-17-one, melting at about 142°–144° and suitable for the following process.

Acetylene gas, scrubbed with water then with sulfuric acid is bubbled into 100 parts by volume of tetrahydrofuran, cooled to 0°–5°, for approximately 30 minutes. The final volume is about 125 parts. To this mixture is then added slowly 25 parts by volume of ethereal 3.1 Molar ethyl magnesium bromide. The resulting suspension is allowed to warm to approximately 10° and a solution of 5.02 parts of the above product and 50 parts by volume of tetrahydrafuran is added. After stirring for approximately 3 hours at room temperature the mixture is cooled in an ice bath and 100 parts by volume of cold saturated aqueous ammonium chloride is added. The mixture is extracted twice with 200 part by volume portions of ether and the extracts are washed with water, then with saturated aqueous sodium chloride. Drying of that solution over anhydrous sodium sulfate followed by removal of the solvent by distillation under reduced pressure affords a residue, which is triturated with hexane to yield a soft solid product. Recrystillization of that material from benzenecyclohexane affords d,1-11$\beta$,18-dimethyl-17$\alpha$-ethynyl-1,4-dihydroestradiol 3-methyl ether, melting at about 161°–164°. Chromatographic purification of the mother liquors and crystallization from benzene-cyclohexane affords an additional quantity of the product.

To a suspension of 2.03 parts of the latter product and 100 parts by volume of methanol is added 1 part of oxalic acid dihydrate dissolved in 10 parts by volume of water. The solution is complete in 15 minutes and after an additional 15 minutes 50 parts by volume of water is again added and the mixture is concentrated under reduced pressure to remove the majority of the methanol. After the addition of 50 parts by volume of 5% aqueous sodium bicarbonate the mixture is extracted with ether and the ether extract is washed successively with water and saturated aqueous sodium chloride. Drying over anhydrous sodium sulfate followed by distillation of the solvent under reduced pressure and trituration of the residue with hexane yields the solid product, melting at about 133°–136°. Recrystallization from benzene-cyclohexane affords d,1-11β-methyl-13-ethyl-17α-ethynylgon5(10)-ene-17β-ol 3-one, melting at about 135°–136°.

EXAMPLE 26

To a solution containing 0.86 part of d,1-11β-methyl-13-ethyl-17α-ethynylgon-5(10)-en-17β-ol-3-one in 30 parts by volume of methanol is added 10 parts by volume of 4 Normal hydrochloric acid and that mixture is stored at room temperature for about 18 hours, at the end of which time 10 parts of water is added. After an additional 2 hours at room temperature the mixture is cooled and the solid filtered and washed well with water. Recrystallization of that crude product from aqueous methanol affords d,1-11β-methyl-13-ethyl-17α-ethynylgon-4-en-17-β-ol-3-one, melting at about 216°–217° and exhibiting an ultraviolet absorption maxima at about 240.5 millimicrons with an extinction coefficient of about 16,700.

EXAMPLE 27

To a solution of 0.909 part of d,1-11β-methyl13-ethyl-17α-ethynylgon-4-en-17β-ol-3-one in 40 parts by volume of tetrahydrofuran is added 2 parts of lithium tri-(tertiarybutoxy)aluminum hydride and the resulting mixture is stirred for approximately 18 hours, at the end of thich time 50 parts by volume of 5% aqueous hydrochloric acid is added. The mixture is extracted with ether and the ether extract is washed successively with water, 5% aqueous sodium becarbonate and water. After drying over anhydrous sodium sulfate the solvent is removed and the residue is purified by chromatography on a silica gel column, followed by crystallization from cyclohexane, thus producing d,1-11β-methyl-13-ethyl-17α-ethynylgon4-ene-3,17β-diol, melting at about 176°–178°.

EXAMPLE 28

To a suspension of 0.244 part of d,1-11β-methyl13-ethyl-17α-ethynylgon-4-ene-3,17β-diol and 0.11 part of 4-dimethylaminopyridine in 5 parts by volume of acetic anhydride is added 5 parts by volume of triethylamine and the resulting reaction mixture is maintained under nitrogen at approximately 40°–45° for about 40 hours, then is cooled and diluted with 20 parts by volume of isopropyl alcohol. The mixture is kept at room temperature for about 30 minutes, then is diluted with 100 parts of water and that aqueous mixture is extracted with ether. The ether extracts are washed successively with water, 5% aqueous sodium bicarbonate, water, and saturated aqueous sodium chloride. Removal of the solvent by distillation under reduced pressure and purification of the residue by chromatography on silica gel affords the crude product, which is further purified by recrystallization from methanol to yield d,1-13β-ethyl-17α-ethynyl11β-methylgon-4-ene-3β,17-diol 3,17-diacetate, melting at about 147°–119° and characterized further by the following structural formula

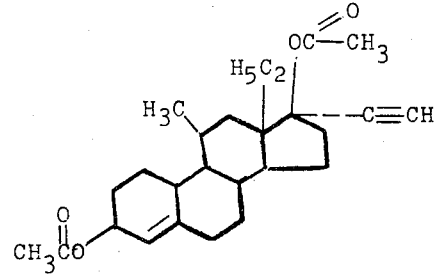

What is claimed is:
1. A process for the manufacture of 11-alkyl steroids which comprises contacting a 6-alkoxy-1-tetralone with a dialkylamino vinylic organometallic reagent, quaternizing the resulting 5-alkoxy-1-(3-dialkylaminoalken-1-yl)-1-tetralol by reaction with an alkyl halide and dehydrating the resulting quaternary ammonium salt by reaction with acetic anhydride or, alternatively, dehydrating said 6-alkoxy-1-(3-dialkylaminoalken-1-yl)-1-tetralol by reaction with acetic anhydride, then quaternizing the resulting 6-alkoxy-1-(3-dialkylaminoalken-2-yl)-3,4-dihydronaphthalene with an alkyl halide, contacting the resulting quaternary salt with a 2-alkylcyclopentane-1,3-dione to yield the corresponding 2-(6-alkoxy-3,4-dihydro-1-naphthyl)-1-(2-alkylcyclopentane-1,3-dione2-yl)-2-alkene, cyclizing the latter product by reaction with p-toluene-sulfonic acid, contacting the resulting 3-alkoxy-11alkylene-13-alkylgona-1,3,5(10),8(9),14-pentaen-17-one with lithium aluminum hydride, reacting the resulting 17β-ol with hydrogen in the presence of a palladium-calcium carbonate catalyst to afford the corresponding 3-alkoxy-11,13β-bisalkylgona-1,3,5,(10 ),9(11), 8(14)-pentaen-17β-ol, contacting the latter product with hydrogen in the presence of palladium on alumina catalyst to yield the corresponding gona-1,3,5(10),8(9)-tetraene, contacting the latter derivative with sodium in liquid ammonia to yield the corresponding gona-1,3,5(10)triene, contacting the latter product with sodium in liquid ammonia in the presence of aniline to afford the corresponding 2,5(10)-diene, contacting that compound with chromic acid to yield the 17-one corresponding, reacting the latter substance with a 1-alkyne to afford the corresponding 17α-alkynyl-17β-ol, hydrolyzing the latter enol ether with oxalic acid to yield the corresponding 5(10)-en-3-one, contacting that product with dilute hydrochloric acid to afford the corresponding 4-en-3-one, contacting that product with lithium tri-tertiary butoxy aluminum hydride to yield the 3β-ol corresponding and reacting that product with acetic anhydride to yield the 3,17-bis-(alkanoate) corresponding.

2. The process of claim 1, wherein the 6-alkoxy-1-tetralone is 6-methoxy-1-tetralone, the dialkylamino vinylic organometallic reagent is 3-dimethylaminopropen-1-yl-2-magnesium bromide, the quaternizing alkyl halide is methyl iodide, the 2-alkylcyclopentane-1,3-dione is 2-ethylcyclopentane-1,3-dione, the 3-alkoxy-11,13-bisalkylgona-1,3,5(10),8-(9),14(15)-pentaen- 17β-ol so produced is 3-methoxy-11-methyl13β-ethyl-gona-1,3,5(10)8(9),14(15)-pentaen-17β-ol, the 3-alkoxy-11,13β-bisalkylgona-1,3,5(10),9(11),8(14)-pentaen-17β-ol is 3-methoxy-11-methyl-13β-ethyl-gona-1,3,5(10),9(11),8(14)-tetraen-17β-ol, the 1-alkyne is acetylene, and the 3,17-bis(alkanoate) is 17β-ethynyl-13β-ethyl-11β-methylgon-4-ene-3β,17β-diol 3-17-diacetate.

* * * * *

UNITED STATES PATENT AND TRADEMARK OFFICE
CERTIFICATE OF CORRECTION

PATENT NO. : 3,962,291

DATED : June 8, 1976

INVENTOR(S) : Robert B. Garland & Raphael Pappo

It is certified that error appears in the above-identified patent and that said Letters Patent are hereby corrected as shown below:

Column 2, line 31, "methoxy-tetralone" should read -- methoxy-1-tetralone --.

Column 2, line 40, "twophase" should read -- two-phase --.

Column 2, line 63, "afford ord" should read -- afford --.

Column 2, line 67, "eoefficients" should read -- coefficients --.

Column 3, line 56, "dihydrophthalene)" should read -- dihydronaphthalene --.

Column 4, lines 4 and 5, "dihydronaphthalene)" should read -- dihydronaphthalene --.

Column 4, line 12, "4dihydronaphthalenemethyl" should read -- 4-dihydronaphthalenemethyl --.

Column 5, line 62, "methylene8" should read -- methylene-8 --.

Column 6, line 18, "amospheric" should read -- atmospheric --.

Column 6, line 23, "material" should read -- methanol --.

Column 6, line 24, "methyl8" should read -- methyl-8 --.

Column 6, line 33, "methyl8" should read -- methyl-8 --.

Column 6, line 33, "bisdehydroestradiol3 should read -- bisdehydroestradiol 3 --.

UNITED STATES PATENT AND TRADEMARK OFFICE
CERTIFICATE OF CORRECTION

PATENT NO. : 3,962,291
DATED : June 8, 1976
INVENTOR(S) : Robert B. Garland & Raphael Pappo It is certified that error appears in the above-identified patent and that said Letters Patent are hereby corrected as shown below:

Column 6, line 40, "dehydroestradio" should read -- dehydroestradiol --.

Column 6, line 49, "skaken" should read -- shaken --.

Column 6, line 56, "11βmethyl" should read -- 11β methyl --.

Column 6, line 63, "parts" should read -- part --.

Column 7, line 11, "methylestradiol3" should read -- methylestradiol-3 --.

Column 7, line 25, "methylestrone3" should read -- methylestrone-3 --.

Column 7, line 53, "methoxy3" should read -- methoxy-3 --.

Column 8, line 28, "dimethyl8" should read -- dimethyl-8 --.

Column 8, line 45, "dehydroestradiol3" should read -- dehydroestradiol-3 --.

Column 9, line 23, "dimethyl8" should read -- dimethyl-8 --.

Column 9, lines 65 and 66, "dimethylestrone3" should read -- dimethylestrone-3 --.

Column 11, line 20, "ethynylgon5" should read -- ethynylgon-5 --.

Column 11, line 40, "methyl13" should read -- methyl-13 --.

UNITED STATES PATENT AND TRADEMARK OFFICE
CERTIFICATE OF CORRECTION

PATENT NO. : 3,962,291
DATED : June 8, 1976
INVENTOR(S) : Robert B. Garland & Raphael Pappo It is certified that error appears in the above-identified patent and that said Letters Patent are hereby corrected as shown below:

Column 11, line 53, "ethynylgon4" should read -- ethynylgon-4 --.

Column 11, line 57, "methyl13" should read -- methyl-13 --.

Column 12, line 6, "ethynyl11" should read -- ethynyl-11 --.

Column 12, Claim 1, line 35, "dione2" should read -- dione-2 --.

Column 12, Claim 1, line 37, "11alkylene" should read -- 11-alkylene --.

Column 13, Claim 2, line 1, "methyl11" should read -- methyl-11 --.

Column 14, Claim 2, line 1, "17β" should read -- 17α --.

Signed and Sealed this

Thirtieth Day of November 1976

[SEAL]

Attest:

RUTH C. MASON
*Attesting Officer*

C. MARSHALL DANN
*Commissioner of Patents and Trademarks*